United States Patent [19]

Cabrera et al.

[11] Patent Number: 5,375,481
[45] Date of Patent: Dec. 27, 1994

[54] MULTI-POSITION RATCHET MECHANISM

[75] Inventors: Rene J. Cabrera, Stoughton;
Francisco A. Amaral, New Bedford;
John J. Amaral, South Dartmouth,
all of Mass.; John R. Bookwalter,
Brattleboro, Vt.

[73] Assignee: Codman & Shurtleff, Inc., Randolph, Mass.

[21] Appl. No.: 152,118

[22] Filed: Nov. 12, 1993

[51] Int. Cl.⁵ .......................... G05G 1/00; A61B 17/02
[52] U.S. Cl. .................................... 74/577 M; 74/535;
74/537; 74/538; 74/540; 74/575; 74/577 R;
128/20; 248/316.4; 248/231.8
[58] Field of Search .................. 74/575, 540, 577 R,
74/577 M, 578, 541, 527, 535–538; 128/20;
248/316.4, 231.8

[56] References Cited

U.S. PATENT DOCUMENTS

| | | | |
|---|---|---|---|
| 3,749,088 | 7/1973 | Gauthier | 74/535 X |
| 3,965,890 | 6/1976 | Gauthier | 128/20 |
| 4,254,763 | 3/1981 | McCready et al. | 128/20 |
| 4,424,724 | 1/1984 | Bookwalter et al. | 74/540 |
| 4,467,791 | 8/1984 | Cabrera et al. | 248/231.8 X |
| 4,834,112 | 5/1989 | Machek et al. | 74/577 M X |
| 4,852,552 | 8/1989 | Chaux | 128/20 |
| 4,865,019 | 9/1989 | Phillips | 128/20 |
| 5,052,373 | 10/1991 | Michelson | 128/20 |
| 5,052,374 | 10/1991 | Jacinto | 128/20 |
| 5,067,477 | 11/1991 | Santangelo | 128/20 |

FOREIGN PATENT DOCUMENTS

| | | | |
|---|---|---|---|
| 670513 | 11/1929 | France | 128/20 |
| 1088710 | 4/1985 | U.S.S.R. | 128/20 |
| 1482675 | 5/1989 | U.S.S.R. | 128/20 |

Primary Examiner—Vinh T. Luong
Attorney, Agent, or Firm—Michael Q. Tatlow

[57] ABSTRACT

A multi-position ratchet mechanism for holding a surgical retractor blade which permits a retractor blade to be rotated into the wound and retracted at the same time to duplicate the natural "toe-in" method of retraction achieved with the hand. The ratchet mechanism includes a ratchet holder to which is pivotally attached a ratchet pivot housing. The retractor blade is mounted in an opening projecting through ratchet pivot housing and held in position by a retractor pawl attached to the ratchet pivot housing. The ratchet pivot housing also has a curved ratchet which depends into a cooperating slot in the ratchet holder and engages a ratchet release bar which is mounted on the ratchet holder and spring biased into the ratchet slot. One end of ratchet release bar is positioned under an actuating surface of the retractor pawl. The application of pressure on the actuating surface will release both ratchets to allow adjustment of the retractor blade.

3 Claims, 4 Drawing Sheets

MULTI-POSITION RATCHET MECHANISM

FIELD OF THE INVENTION

The present invention relates to a multi-position ratchet mechanism for holding a surgical retractor blade and, more particularly, to a quick-release ratchet mechanism which permits the retractor blade to be tilted into the wound and retracted at the same time. A single thumb piece can be manipulated to permit simultaneous in and out motion of the retractor blade and tilting of the retractor blade.

BACKGROUND OF THE INVENTION

In surgical operations of the chest or abdomen, it is customary to employ a retraction apparatus to retain tissue away from the operative site. Such a retractor system is shown in U.S. Pat. Nos. 4,254,763, and in 4,424,724. The retractor shown in U.S. Pat. No. 4,424,724 is a multi-position ratchet mechanism which permits a retractor blade to be rotated into the wound and retracted at the same time to duplicate the natural toe-in method of retraction achieved if the retractor was held by hand. These ratchet mechanism are employed in a surgical retractor assembly which includes a support post which attaches directly to the surgical operating table. An extension arm may be attached to the support post for supporting an oval or round or other shape ring above the surgical incision. One or more retractor blades can be attached to the ring by means of the retractor ratchet mechanisms. Retractor blades of different sizes and shapes may be used to obtain the desired positioning and retraction of internal organs and tissue so that the operative site may be completely exposed for the surgeon. In the retractor system shown in the U.S. Pat. No. 4,424,724, the retractor can be rotated by tilting the blade into the wound so that organs can be retracted and lifted at the same time. It is particularly advantageous to be able to retract toward the ring to obtain exposure under an organ, such as lifting on the thoracic cage to reach a hiatal hernia. By rotating the blade down into the wound, and then lifting and retracting at the same time, one duplicates the natural "toe-in" method of retraction that would be achieved by the hand. This type of retraction enables the surgeon to see the underlying organs better than if the retractor can only move away from the operative site without lifting. The ability to lift the retractor blade also enables a single retractor blade to be used at different depth rather than to use different retractor blades for different depths in the body.

The retractor ratchet system shown in U.S. Pat. No. 4,424,724 employs two ratchet mechanism to allow the tilting movement and the movement of the retractor blade stem in an out of the operative area of the patent. In order to adjust the ratchet mechanism two pawls in two different positions on the ratchet mechanism must be activated. It is therefore difficult to adjust both the tilting of the retractor and the position of the retractor blade at the same time. In order to move the reactor blade in and out of the wound area, one ratchet must be disengaged by applying pressure on a ratchet release mechanism and then moving the blade to the desired position. In order to tilt the ratchet mechanism, a second activating mechanism must be depressed to disengage a second ratchet. Because of the relative positions of these two disengagement mechanisms, it is cumbersome to disengage both mechanisms with one hand. It would be advantageous to have a ratchet mechanism in which both the tilt and the movement of the retractor blade in and out of the wound site could be controlled with a single lever to simultaneously release both ratchets so that the retractor blade could be positioned easily.

SUMMARY OF THE INVENTION

The present invention provides a quick release multi-position ratchet mechanism where both the tilting and in and out ratchets can be released by depressing the same release lever and the retractor blade can be readily positioned by a single individual in the operating room.

DETAILED DESCRIPTION OF THE PREFERRED EMBODIMENT

Figure 1:
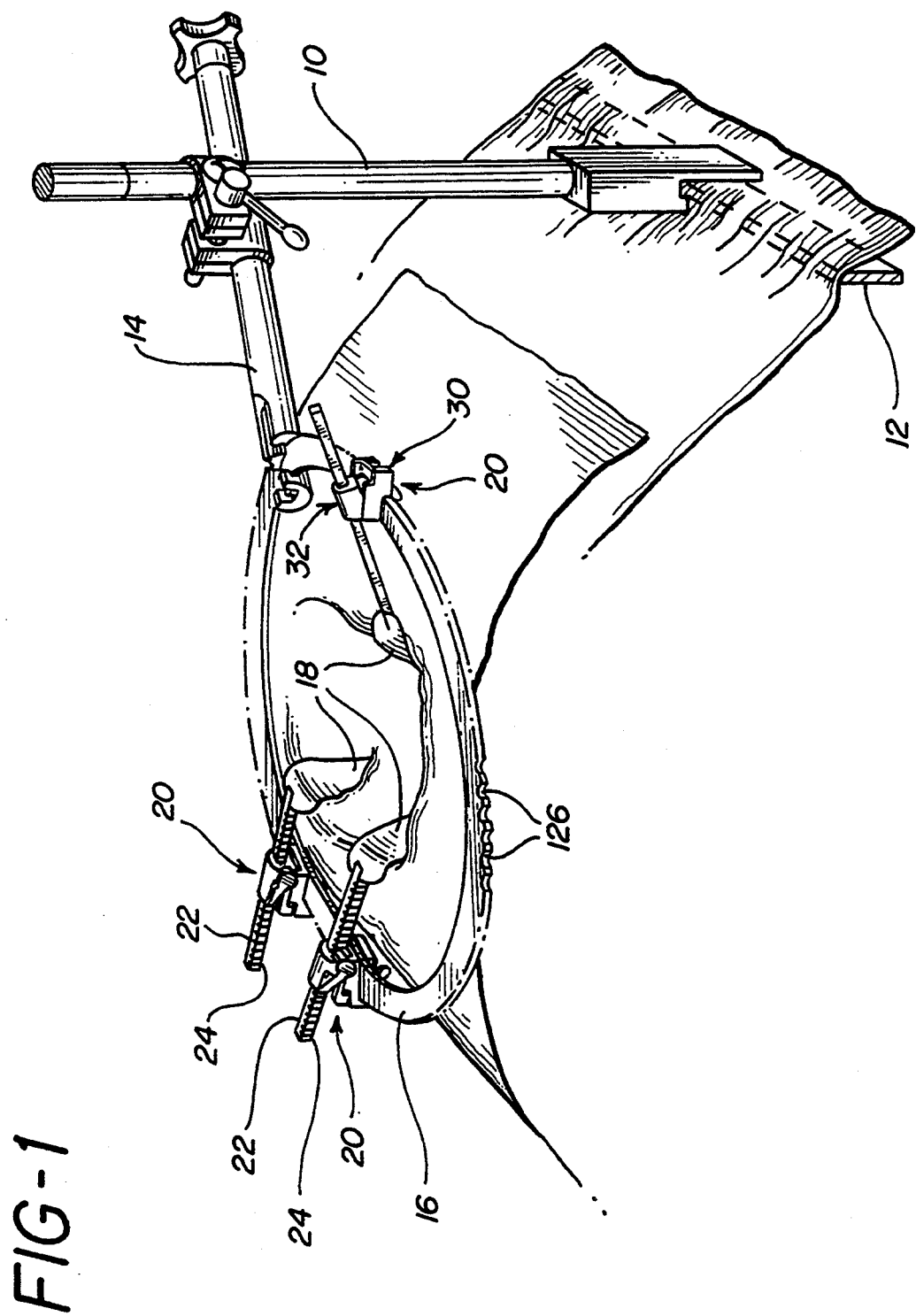
FIG. 1 shows a perspective view of the entire retractor assembly with which the multi-position ratchet mechanism of the present invention is used.

Referring now to FIG. 1, there is shown a surgical retractor assembly similar to that shown in U.S. Pat. No. 4,254,763. A vertical support post 10 is clamped to the side rail 12 of an operating table on which the patient is supported. A horizontal arm 14 extends horizontally over the patient and supports a support ring 16 on which a number of retractor blades 18 are supported by ratchet mechanisms 20. Each retractor blade 18 includes a generally rectangular stem 22 along one side of which is included a ratchet 24. Retractor blades 18 extend into the wound cavity. The ratchet mechanism of the present invention and the ratchet mechanism disclosed in U.S. Pat. No. 4,424,724 allow the surgeon to retract and lift an organ at the same time to duplicate the natural "toe-in" method of retraction one achieves by hand.

Figure 3:
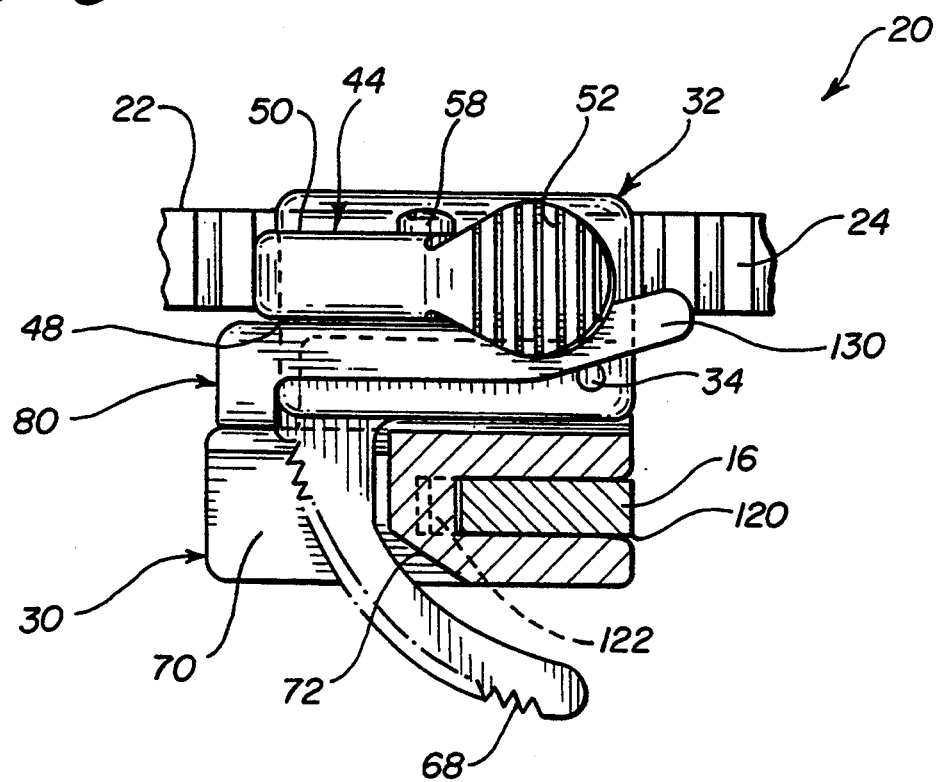
FIG. 3 shows a side elevation, partly in section, of the assembled mechanism shown in FIG. 2 together with the retractor blade stem.
Figure 4:
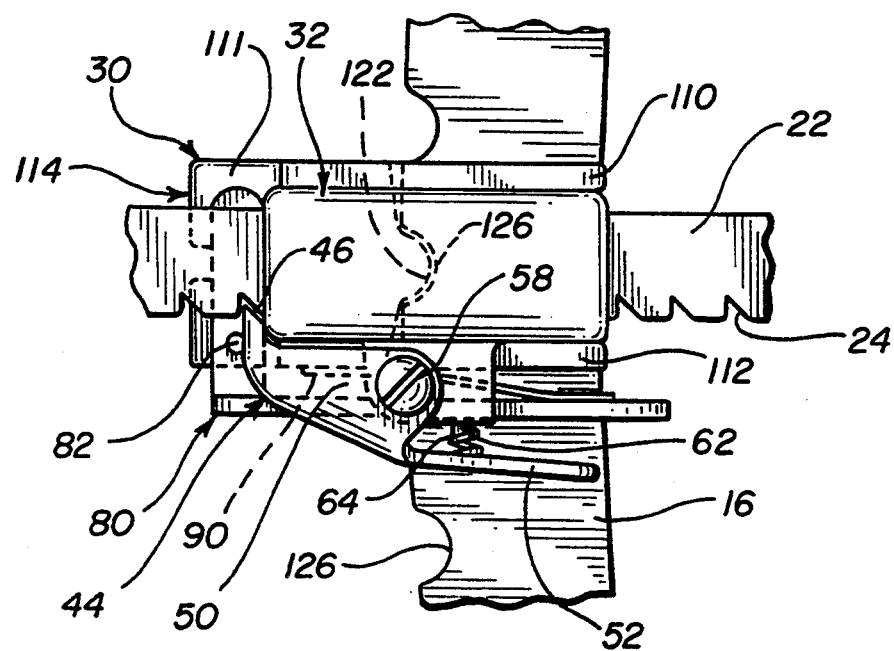
FIG. 4 shows a top plan view of the assembled mechanism shown in FIG. 2 together with a portion of the ring holder.
Figure 5:
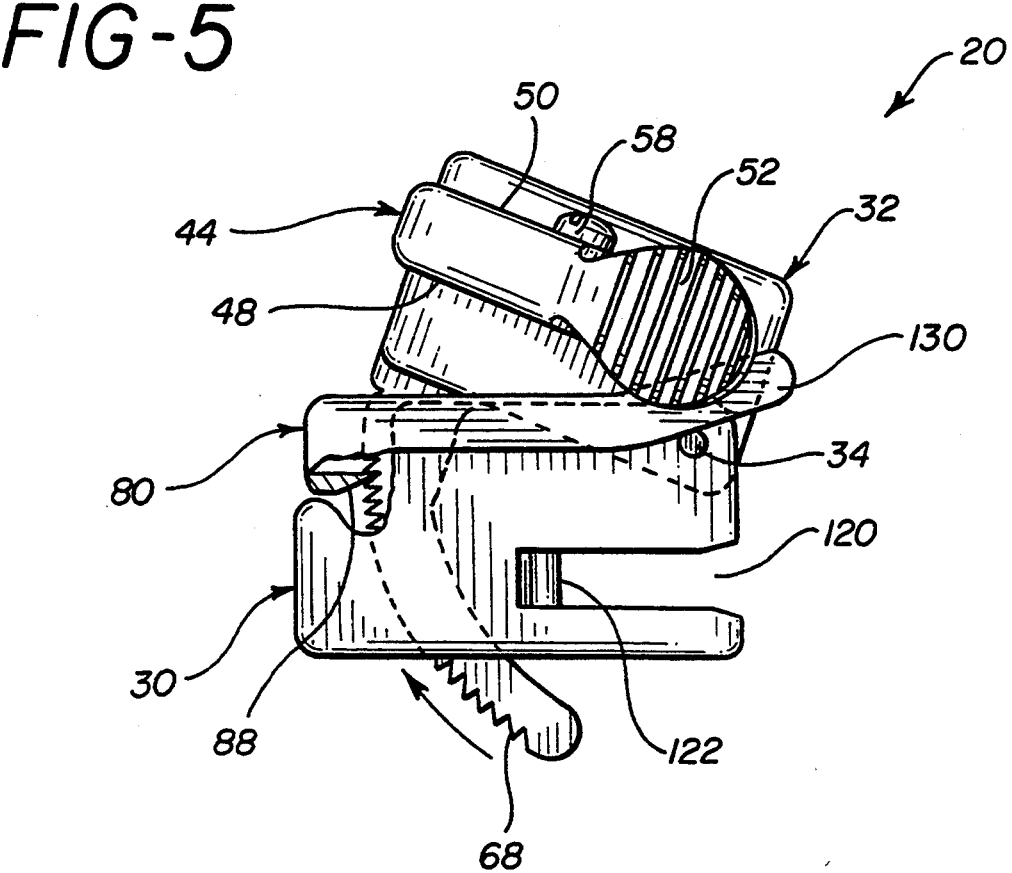
FIG. 5 shows a side view of the ratchet mechanism of the present invention.
Figure 6:
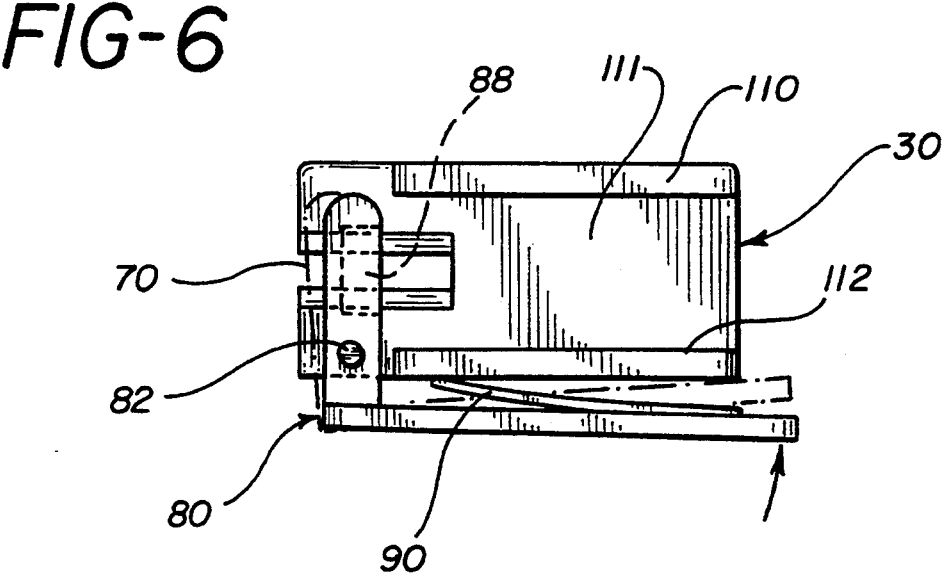
FIG. 6 shows a top view of the ratchet holding mechanism of the present invention.

The components of the present multi-position ratchet mechanism 20 are similar to the ratchet mechanisms shown in U.S. Pat. No. 4,424,724. The differences in the components will become apparent. The mechanism will be described in connection with FIG. 2. The working of the mechanism will be described in connection with the support shown ring as shown in FIGS. 1, 3 and 4.

Figure 2:
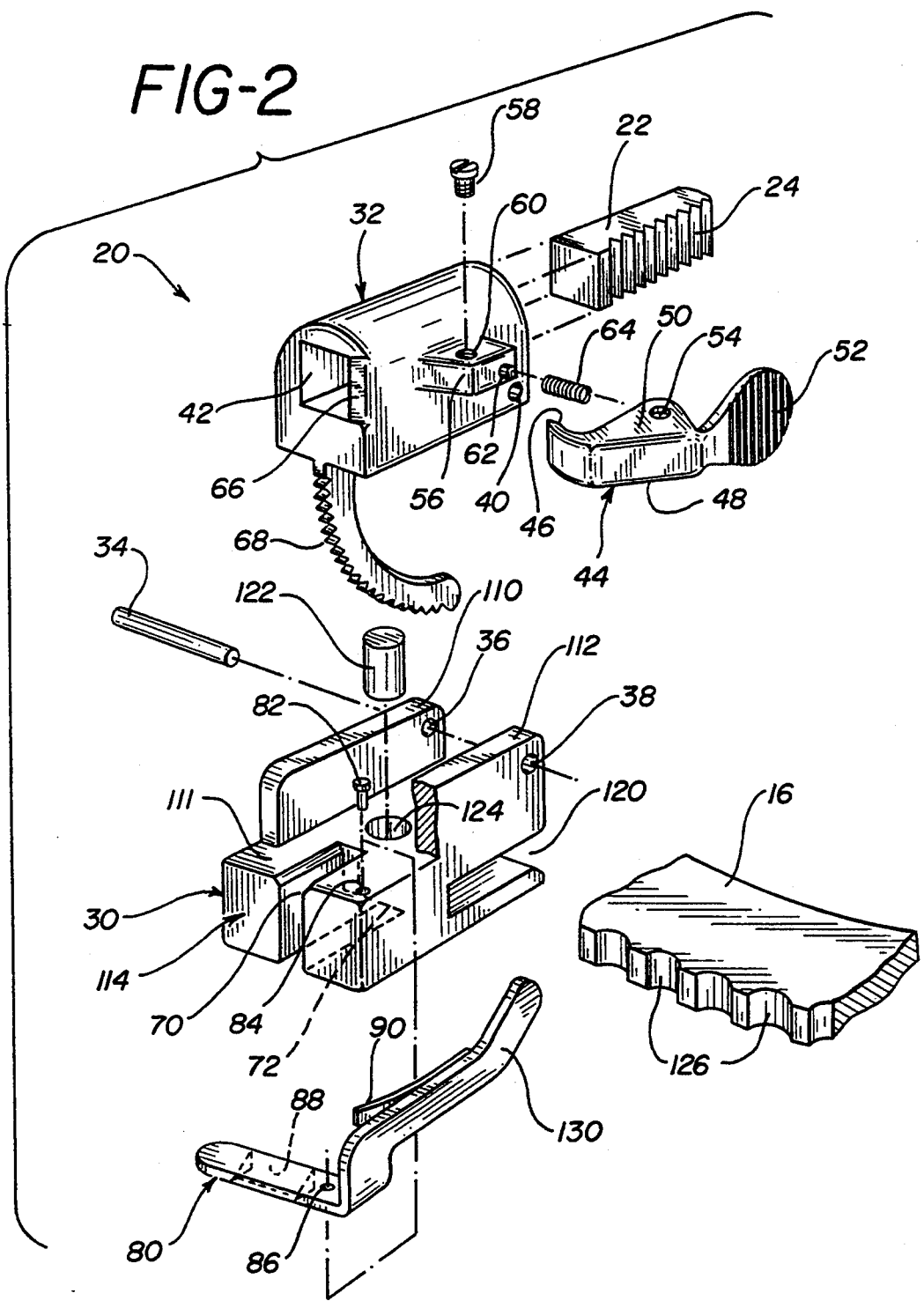
FIG. 2 shows an exploded perspective view of the multi-position ratchet mechanism of the present invention.

Referring now to FIG. 2, there is shown the multi-position ratchet mechanism 20 which includes a generally rectangular ratchet holder 30 to which a ratchet pivot mechanism 32 is pivotally attached by means of a pin 34 extending through bores 36 and 38 in ratchet holder 30 and bore 40 in ratchet pivot housing 32. A generally rectangular bore 42 extends completely through ratchet pivot housing 32 to receive the generally rectangular retractor blade stem 22. There is a ratchet 24 is disposed on one side of retractor blade stem 22. Retractor pawl 44 includes a pawl blade 46, left and right skirts 48 and 50 and actuating surface or thumb piece 52. Each of skirts 48 and 50 includes a bore 54. Retractor pawl 44 is mounted to a boss 56 extending from the side of ratchet pivot housing 32 by means of a screw 58 which projects through bores 54 and bore 60 in boss 56. Boss 56 has a projected portion 62 on which is affixed a bias spring 64 for biasing retractor pawl blade 46 into close engagement with ratchet 24 on retractor blade stem 22. A corner 66 of ratchet pivot housing 32 is cut away to provide clearance for ratchet pawl blade 46.

A curved ratchet 68 depends from the bottom of the ratchet pivot housing 32 toward ratchet holder 30. The rear surface 114 of ratchet holder 30 includes a vertical slot 70 which receives curved ratchet 68. The interior transverse wall 72 of slot 70 is curved to the same extent as curved ratchet 68 so that curved ratchet 68 may slide easily in and out of slot 70 as ratchet pivot housing 32 pivots about pivot pin 34.

The top surface 111 of ratchet holder 30 includes left and right side walls 110 and 112 which extend along ratchet holder 30. Side walls 110 and 112 are spaced apart a sufficient distance to permit ratchet pivot housing 32 to pivot between them with a clearance fit to provide lateral stability to the ratchet pivot housing 32. Side walls 110 and 112 extend along the top surface of the ratchet holder 30 a distance equal to the length of the ratchet pivot housing 32. Ratchet holder 30 includes a transverse slot 120 which permits ratchet holder 30 to slide onto the support ring 16 shown in FIG. 4. Slot 120 extends from the front face of ratchet holder 30 toward the rear face, a distance less than the width of ring 16. Dowel pin 122 fits with a tight fit into bore 124 such that the circumferential edge of dowel pin 122 projects into slot 120. When the ratchet holder 30 is slid onto ring 16, the circumferential edge of dowel pin 122 engages on one of the indentations 126 on the outer circumferential edge of ring 16. The interaction of indentations 126 and the edge of dowel pin 122 provide a means for fixing the circumferential position of ratchet holder 30 along the ring 16. Alternatively, bore 124 and pin 122 may be replaced by a rounded projection molded or cast into the rear wall 121 of slot 120. The tension of the retractor blade against the retracted organ pulls retractor holder forward so that the edge of dowel pin 122 engages the indentations 126 on the ring 16 to prevent circumferential sliding of the ratchet holder 30 and to prevent the ratchet holder 30 from falling from the ring 16. The interaction of dowel pin 122 with indentations 126 is best seen in FIG. 4.

There is a ratchet release bar 80 which is affixed to the top surface of the ratchet holder 30 adjacent the slot 70. The ratchet release bar 80 is affixed by a pin 82 which extends through bore 86 and is retained in a bore 84 in the body of the ratchet holder. The ratchet release bar 80 has thumb piece 130 which is generally L-shaped. There is a cut out portion 88 on one side of the ratchet release bar to engage with the ratchet 68 on the ratchet pivot housing 32. When the cut out portion 88 engages the teeth in the ratchet 68, the ratchet pivot housing is fixed in position.

The ratchet release bar 80 extends along one side of the ratchet holder and extends to a position under the actuating thumb piece 52 attached to the ratchet housing 32. There is a bar spring 90 which is attached to the side of the ratchet release bar 80 facing the ratchet pivot housing which biases the release bar 80 so that the bar 80 is engaged with the curved ratchet 68 on the ratchet pivot housing and retains the ratchet pivot housing in the locked position. The end of the ratchet release bar 80 preferably extends beyond the end of the actuating thumb piece 52 on the ratchet pivot housing. This is to allow the operator of the unit to engage the end of the ratchet release bar 80 alone by exerting pressure on that portion of the release bar that extends beyond the actuating thumb piece 52 on the ratchet pivot housing 32. If the operator wishes to release both ratchets at the same time it is only necessary to exert pressure on the actuating thumb piece 52 which will release the blade 46 from ratchet 24 and at the same time release the release bar 80 from the curve ratchet 68. This allows one hand adjustment of the retractor. It also avoids a problem of the surgeon having to consider which of the thumb pieces must be depressed in order to elevate the blade or to move the blade in and out. This ratchet release mechanism also allows the surgeon to adjust the retractor without taking his eyes away from the operative field.

The assembled multi-position ratchet mechanism 20 of the present invention is shown in FIGS. 1, 3, and 4. The position of retractor blade stem 22 and ratchet pivot housing 32 is clearly shown in FIG. 4 with pawl blade 46 engaging ratchet 24 on the side of retractor blade stem 22. As blade stem 22 is withdrawn through the opening 42 in ratchet pivot housing 32, spring-loaded pawl 44 will hold retractor blade stem 22 in position through the cooperative action of pawl blade 46 and the ratchet 22. It can be seen best in FIG. 3 that the pivot angle of ratchet pivot housing 32 with respect to ratchet holder 30 can easily be adjusted by grasping the retractor blade stem 22 and merely pivoting it with respect to ratchet holder 30.

As the ratchet pivot housing 32 is pivoted around pivot pin 34, curved ratchet 68 will move in relation to the ratchet release bar 80. The undercut region 88 of the ratchet release bar 80 will engage the teeth on the ratchet. Exerting pressure on the ratchet release bar will pivot the bar away from the ratchet and allow the ratchet to be pivoted to the desired position.

It can be seen that multi-position ratchet mechanism 20 of the present invention permits a retractor blade 18 to be rotated into a wound in a relatively easy fashion by exerting pressure on the actuating thumb piece 52, which will in turn will exert pressure on the end of the ratchet release bar 80 which will allow the retractor blade stem 24 to be moved in or out of the wound area and at the same time allow the ratchet pivot to be pivoted in or away from the would. This allows the operator to duplicate the "toe-in" method of retraction achieved by hand.

The present invention has been described in conjunction with the preferred embodiment. Those skilled in the art will appreciate that other modifications and changes may be made in the present embodiment without departing from the present invention.

We claim:

1. In a multi-position ratchet mechanism comprising;
   a generally rectangular ratchet holder having top, bottom, front, rear, left and right surfaces, a pivot ratchet housing pivotally mounted on said ratchet holder;
   a bore extending through said ratchet pivot housing to receive a retractor blade stem; said retractor blade stem having a ratchet on a surface of said stem;
   a pawl pivotally affixed to said ratchet housing and having a pawl blade at one end to engage the ratchet on said retractor blade stem, and an actuating surface at a second end to pivot the pawl blade out of engagement with said retractor blade stem ratchet when force is applied to said actuating surface;

a slot on said ratchet holder extending from its rear surface toward its front surface and extending from said top to said bottom surface;

a curved pivot ratchet integral with and depending from said ratchet pivot housing into said slot of said ratchet holder;

means attached to said ratchet holder for biasing said pivot pawl into engagement with said pivot ratchet;

the improvement comprising a ratchet release bar pivotally affixed on the top surface of said ratchet holder and extending into said slot on said ratchet holder;

said ratchet release bar having a surface positioned to engage said curved ratchet, and a second surface extending along the ratchet housing and underlying the actuating surface of said pawl, whereby the movement of said actuating surface will release the pawl blade engaging the ratchet on the retractor blade stem and the ratchet release bar engaging the curved ratchet.

2. The ratchet mechanism of claim 1 including means to bias the ratchet release bar into engagement with said curved ratchet.

3. The ratchet mechanism of claim 1 in which one end of the ratchet release bar extends beyond the end of the actuating surface of said pawl blade.

* * * * *